United States Patent [19]

Baines et al.

[11] 4,036,950

[45] July 19, 1977

[54] ORAL PREPARATIONS

[75] Inventors: Eric Baines, Flixton; Sydney James Forshaw, Failsworth; Kenneth Harvey, Wilmslow, all of England

[73] Assignee: Colgate-Palmolive Company, New York, N.Y.

[21] Appl. No.: 645,744

[22] Filed: Dec. 31, 1975

[30] Foreign Application Priority Data

Jan. 15, 1975 United Kingdom .............. 1797/75

[51] Int. Cl.² .......................... A61K 7/18; A61K 7/22
[52] U.S. Cl. ........................ 424/54; 424/52; 424/57
[58] Field of Search ...................... 424/49–58

[56] References Cited

U.S. PATENT DOCUMENTS

| | | | |
|---|---|---|---|
| 3,060,098 | 10/1962 | Gerson | 424/52 |
| 3,662,060 | 5/1972 | Clippendale et al. | 424/57 |
| 3,670,076 | 6/1972 | Muhler | 424/49 |
| 3,678,155 | 7/1972 | Clippendale et al. | 424/49 |
| 3,842,168 | 10/1974 | Colodney | 424/54 |
| 3,843,779 | 10/1974 | Norfleet | 424/54 |
| 3,887,701 | 6/1975 | Nachtigal | 424/54 |
| 3,925,543 | 12/1975 | Donohue | 424/52 |
| 3,937,805 | 2/1976 | Harrison | 424/52 |
| 3,956,478 | 5/1976 | King et al. | 424/52 |
| 3,957,968 | 5/1976 | Cordon | 424/49 |

*Primary Examiner* — Shep K. Rose
*Attorney, Agent, or Firm* — Robert L. Stone; Murray M. Grill; Herbert S. Sylvester

[57] ABSTRACT

An oral preparation comprising a dentally acceptable oral vehicle and dispersed therein a cationic antibacterial agent in amount of about 0.01–5% by weight based on the cationic portion thereof and about 0.05–5% by weight of an anionic phosphate ester surface active agent comprising a mixture of monoester of the formula

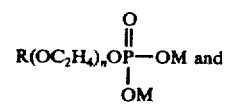

diester of the formula

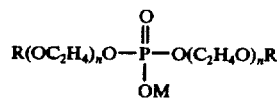

wherein R is an alkyl group of 10–20 carbon atoms, $n$ an integer from 1–6 and M is selected from the group consisting of hydrogen, alkali metal and ammonium, said oral preparation having a pH of at least 6.

15 Claims, No Drawings

ORAL PREPARATIONS

This invention relates to oral preparations.

Oral preparations have been prepared in the past ing 2-ethylhexyl groups instead of chlorophenyl groups (Sterwin 904) and other bisbiguanides such as those described in German Patent Application No. P 2,332,383 published Jan. 10, 1974 which sets forth the following formula:

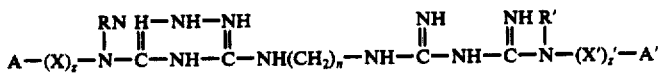

which contain cationic antibacterial agents. Such agents have been recommended for such preparations. Due to their ability to inhibit the growth of many microorganisms such as Staphylococcus aureus, Streptococcus mutans, and Lactobacillus acidophilus odontolyticus. However, in the presence of various components commony employed in oral preparations, they have been observedto have diminished antibacterial effectiveness. Such components are those which, in particular, provide anions, such as anionic foaming surface-active agents, e.g., sodium lauryl sulphate.

It is an advantage of this invention that an oral preparation is provided which contains cationic antibacterial agent and an anionic foaming surface active agent which does not substantially diminish the antibacterial effectiveness of the cationic agent. Other advantages will be apparent from consideration of the following specification.

In accordance with certain of its aspects, this invention relates to an oral preparation comprising a dentally acceptable oral vehicle and dispersed therein a cationic antibacterial agent in amount of about 0.01-5% by weight based on the cationic portion thereof and about 0.05-5% weight of an anionic phosphate ester surface active agent comprising a mixture of monoester of the formula

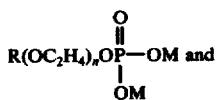

diester of the formula

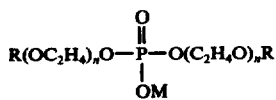

wherein R is an alkyl group of 10-20 carbon atoms, $n$ an integer from 1-6 and M is selected from the group consisting of hydrogen, alkali metal and ammonium, said oral preparation having a pH of at least about 6.

Cationic antibacterial materials are well known in the art. See, for instance the section on "Quaternary Ammonium and Related Compounds" in the article on "Antiseptics and Disinfectants" in Kirk-Othmer *Encyclopedia of Chemical Technology* second Edition (Vol. 2 p. 632-635), incorporated herein by reference. Among the most common of these are germicidal quaternary ammonium compounds such as benzethonium chloride; others of this class (and generic formulas and descriptions thereof) are those mentioned, for instance, in U.S. Pat. Nos. 2,984,639; 3,325,402; 3,703,583; and 3,431,208 and British Pat. No. 1,319,396. Usually, one of the substituents on the quaternary nitrogen has a chain length of some 8 to 18 carbon atoms. Other types are the amidines such as the substituted quanidines e.g. chlorohexidine (Hibitane) and the corresponding compound hav- in which A and A' signify as the case may be either (1) a phenyl radical, which as substituent can contain up to 2 alkyl or alkoxy groups with 1 up to about 4 C-atoms, a nitro group or a halogen atom, (2) an alkyl group which contains 1 to about 12 C-atoms, or (3) alicyclic groups with 4 to about 12 C-atoms, X and X' as the case may be represent in alkylene radical with 1-3 C-atoms, z and z' are as the case may be either zero or 1, R and R' as the case may be, represent either hydrogen, an alkyl radical with 1 to about 12 C-atoms or an aralkyl radical with 7 to about 12 C-atoms, $n$ is a whole number of 2 to inclusively 12 and the polymethylene chain $(CH_2)_n$ can be interrupted by up to 5 ether, thioether, phenyl- or naphthyl groups, or the pharmaceutically suitable salts thereof. The antibacterial compound is preferably one which has an antibacterial activity such that its phenol coefficient is well over 50, more preferably well above 100, such as above about 200 or more for S. aureus; for instance the phenol coefficient (A.O.A.C.) of benzethonium chloride (Hyamine 1622) is given by the manufacturer as 410, for S. aureus. The cationic antibacterial agent will generally be a monomeric (or possibly dimeric) material of molecular weight well below 2,000, such as less than about 1,000. It is, however, within the broader scope of the invention to employ a polymeric cationic anitbacterial agent. The cationic antibacterial agent is preferably supplied in the form of an orally acceptable salt thereof, such as the chloride.

Further anitbacterial agents which are employed in thepractice of this invention are quaternary ammonium halides such as those of the formula

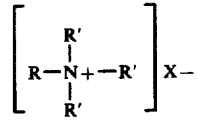

wherein R is a long chain alkyl group having 10-18 carbon atoms, R' is a alkyl group having 1-3 carbon atoms and X is a haologen, such as chlorine, bromine and iodine. Cetrimide, which is a mixture of dodecyl, tetradecyl and hexadecyl trimethyl ammonium bromide is a particularly desirable example of the quaternary ammonium halide antibacterial agents.

The most highly preferred antibacterial agent employed in the practice of this invention is chlorhexidine, i.e., 1,6-de-(p-chlorophenyl biguanido) hexane. It is particularly preferred to use water-soluble salts thereof, such as the digluconate and diacetate salts.

About 0.01-5% by weight of antibacterial agent (based on cationic portion thereof) is provided to the oral preparation, preferably about 0.05-1.0% and most preferably about 0.4-0.5%.

The anionic phosphate esters are mixtures of mono and di-esters of the formulas hereinabove set forth. They are available from MoDo Kemi Aktiebolaget, formerly Berol Aktiebolaget, of Sweden under the name Berol and may include an anionic triester moiety to, as well as some non-ionic portion. Berol 729 has alkyl chain lengths of 16–18 carbon atoms and contains series of 4 ethylene oxide units. Since the acid form of Berol 729 typically provides a completed oral preparation with a pH below 6, this material is generally used in neutralized or partially neutralized form in order to assure a pH above about 6 to the completed oral preparation.

Further anionic phosphate esters which may be used in acid or neutralized forms are Berol 525 which contains alkyl groups of 10–18 carbon atoms and series of 5 ethylene oxide units and Berol 513 which contains alkyl groups of 16–18 carbon atoms. However, use of Berol 525 may also provide a completed oral preparation with a pH below 6 and it is preferred to use it in neutralized or partially neutralized form. Further Berol anionic phosphate esters are available as Berol 521, Berol 724 and Berol 733. The weight ratio of mono-ester to di-ester may vary, typically from about 1:10 to 10:1.

When the acid of the anionic phosphate ester surface active agents are neutralized or partially neutralized, alkali metal, preferably sodium, or ammonium cations are present. The surface active agent is employed in the oral preparation in amount of about 0.05–5% by weight, preferably about 0.5–3.0% and most preferably about 1–2%.

In certain forms of this invention, the oral preparation may be substantially solid or pasty or gel in character, such as a tooth powder, dental tablet or most preferably a tooth paste or dental cream or gel. The dental vehicle of such preparations typically comprises a dentally acceptable water-insoluble polishing material. The preferred polishing materials are nonionic in character, such as alpha-alumina trihydrate, calcined alumina, crystalline silica, and dehydrated silica gel including mixtures thereof. When employed, crystalline silica has particle sizes up to about 5 microns, a mean particle size of up to 1.1 microns and a surface area of up to 50,000 $cm^2/gm$. However, other polishing materials which are salts may also be additionally or alternatively used. These include water-insoluble sodium metaphosphate (preferably substantially free of water-solubles content) tricalcium phosphate, calcium pyrophosphate, magnesium orthophosphate, trimagnesium phosphate, calcium carbonate, aluminium silicate, zirconium silicate, bentonite and mixtures thereof.

The most preferred polishing material is alumina, particularly hydrated alumina, for instance, as sold by Alcoa as C333 or by British Aluminium Co. a AF260.

When visually clear gels are desired, a polishing agent of colloidal silica, such as those sold under the trademark SYLOID as Syloid 72 and Syloid 74 and complex alkali metal aluminosilicate (preferably with under 1% by weight contents of N $Na_2O$ and $Al_2O_3$) are particularly useful, since they have refractive indices close to the refractive indices of gelling agent-liquid (including water and humectant) systems commonly used in dentifrices.

The polishing material is generally present in amounts of about 5–99% by weight of an oral composition containing it; about 5–50% being typical and about 10–30% being preferable for a visually clear gel dentifrice; about 20–75% being typical and about 30–55% being preferable for an opaque toothpaste; and about 70–99% being typical and about 75–95% being perferable for a tooth powder or dental tablet.

In the preparation of tooth powders, it is usually sufficient to admix mechanically e.g., by milling, the various solid ingredients in appropriate quantities and particle sizes.

In the preparation of dental tablets, polishing and binding agents are mixed and additional components then added. The composition is then blended in a powder mixer and fed to a tablet press.

In pasty and gel oral preparations, the liquid vehicle may comprise water, typically in amount of about 10–90% by weight of the preparation. The liquid vehicle may additionally or alternatively comprise humectants such as glycerine, sorbitol solution or propylene glycol. A mixture of water and glycerine and/or sorbitol solution is particularly advantageous. Visually clear gels preferably contain about 10–30% by weight of water, 0 to about 80% by weight of glycerine, and about 20–80% by weight by sorbitol. Opaque paste preferably contain about 20–30% by weight of humectant 0 to about 45% by weight of water.

The solid portion of the vehicle of a pasty or gel composition is a gelling agent or binder such as hydroxyethyl cellulose and hydroxypropyl cellulose. These gelling agents are particularly preferred since they do not provide ions to the composition. Other gelling agents which may be used include Irish moss, gum tragacanth, sodium carboxymethyl cellulose, polyvinyl pyrrolidone, starch and water-soluble hydrophilic colloidal carboxyvinyl polymers such as those sold under the name Carbopol 934 and 940. When sodium carboxymethyl cellulose is employed and the cationic antibacterial agent is a biguanido hexane, care should be taken in formulating the dentifrice to avoid precipitation and flocculation of the components, in accordance with the techniques set forth in British Pat. Nos. 1,344,042 and 1,344,044.

A toothpaste or gel is generally placed in an extrudable tube such as a lined lead or a lined or unlined aluminum tube or an aerosol can, for eacy application to a toothbrush.

In certain other forms of this invention, the oral preparation may be substantially liquid in character such as a mouthwash or rinse. In such a preparation the vehicle is typically a water-alcohol mixture. Generally, the ratio of water to alcohol is in the range of about 1:1 to 20:1, preferably about 3:1 to 20:1. The total amount of water-alcohol mixture in this type of preparation is typically about 70–99.9% by weight.

The oral preparations may include an organic surface active agent in addition to the anionic phosphate ester surface active agent. Preferably, such additional agent is nonionic in nature such as condensation of sorbitan monostearate with approximately 60 moles or ethylene oxide, condensates of ethylene oxide with propylene glycol (available under the trademark "Pluronics") and amphoteric agents such as quaternized imidazole derivatives which are available under the trademark "Miranol" such as Miranol C2M. It is preferred that the total amount of surface active agent not exceed about 5% by weight of the oral composition. At least about 0.05% of the oral composition should be composed of the anionic phosphate ester surface active agent.

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as suitable alkali metal, alkaline earth metal, and heavy metal salts, for example, sodium fluoride, potassium fluoride, ammonium fluoride, a copper fluoride such as cuprous fluoride, zinc fluoride, a tin fluoride such as stannic fluoride, or stannous chlorofluoride, barium fluoride, sodium fluorosilicate, ammonium fluorosilicate, sodium fluorozirconate, sodium monofluorophosphate, aluminum mono-and di-fluorophosphate, and fluorinated sodium calcium pyrophosphate. Alkali metal and tin fluorides, such as sodium and stannous fluorides and mixtures thereof, are preferred.

The amount of the fluorine-providing compound is dependent to some extent upon the type of compound, its solubility, and the type of oral preparation, but it must be a non-toxic amount. In a solid oral preparation, such as a toothpaste or toothpowder, it is considered that an amount of such compound which releases a maximum of 1% by weight, based on the weight of the preparation, is satisfactory. Any suitable minimum amount of such compound may be used, but it is preferable to employ sufficient compound to release from 0.005 to 1%, most preferably about 0.1%, by weight of fluoride ion. Typically, in the cases of alkali metal fluoride and stannous fluoride, this component is present in an amount up to 2% by weight, based on the weight of the preparation, and preferably in the range of from 0.05 to 1%. In the case of sodium monofluorophosphate the compound may be present in amount up to 7.6% by weight, more typically 0.76%.

In a liquid oral preparation such as a mouthwash, the fluorine-providing compound is typically present in an amount sufficient to release up to 0.13%, preferably from 0.0013 to 0.1% and most preferably from 0.0013 to 0.05% by weight of fluoride ion.

Various other materials may be incorporated in the oral preparations of this invention. Examples are coloring or whitening agents, preservatives, silicones, chlorophyll compounds, and ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening materials may also be employed. Examples of suitable flavoring constituents are flavoring oils, e.g., oils of spearmint, peppermint, wintergreen, sassafras, clove, sage, eucalyptus, marjoram, cinnamon, lemon, and orange, and methylsalicylate. Suitable sweetening agents incude sucrose, lactose, maltose, sorbitol, sodium cyclamate, perillartine, and saccharin, Suitably, flavour and sweetening agent may together comprise from 0.01 to 5% more of the preparation.

The oral preparation should have a pH of at least about 6, preferably about 6–10. When reference is made to the pH herein, it is intended that the pH determination be made directly on the oral preparation, unless it is a solid, such as a toothpowder, in which case it is made on a 20% slurry thereof.

Pasty or gel oral compositions are typically prepared by dispersing polishing material in the dental vehicle and adding the phosphate ester and other components thereto.

The following specific examples are futher illustrative of the nature of the present invention although it is understood that the invention is not limited thereto. All amounts are by weight unless otherwise indicated.

EXAMPLE 1

Dentifrices having the following formulation are prepared:

| Components | Parts |
| --- | --- |
| Glycerine | 20.0 |
| Hydroxyethyl cellulose | 1.3 |
| Sodium saccharine | 0.2 |
| Titanium dioxide | 0.5 |
| Alpha alumina trihydrate (British Aluminum AF260) | 51.5 |
| 1,6-di-(p-chlorophenyl biguanido) hexane digluconate (20% solution) | 4.723 |
| Phosphate ester (as indicated below) | 1.5 |
| Flavour | 1.0 |
| Water | Q.S. to 100 |

The following Berol phosphate esters are employed: Berol 513-acid form (Dentifrice pH 6.3); Berol 513-fully neutralized form (Dentifrice pH 10.0); Berol 729 fully neutralized form (Dentifrice pH 9.1) Berol 521 - acid form (Dentifrice pH 9.5)

As the Berol phosphate esters are varied, the pH of the dentifrice also varies above 6.0. Similar effects are observed when fully neutralized Berol 525 and fully neutralized Berol 521 are employed.

The formulation is also prepared with Alcoa C333 as the alpha alumina trihydrate.

All dentifrices exhibit desirable antibacterial activity on *Streptococcus mutans* and have good foaming characteristics.

EXAMPLE 2

The following dentifrice also exhibits desirable antibacterial activity and has foaming characteristics:

| Components | Parts |
| --- | --- |
| Glycerine | 20.0 |
| Hydroxyethyl cellulose | 1.3 |
| Sodium saccharine | 0.2 |
| Alpha-alumina trihydrate | 31.5 |
| Calcined alumina | 20.0 |
| 1,6-di-(p-chlorophenyl biguanido) hexane digluconate (20% solution) | 3.778 |
| Berol 513 (pH 6.0) - partially neutralized form | 1.65 |
| Flavour | 1.0 |
| Water | Q.S. to 100 |
| Dentifrice pH 7.38 | |

EXAMPLE 3

The following dentifrice again exhibits antibacterial activity and has good foaming characteristics and is also effective to reduce the solubility of dental enamel:

| Components | Parts |
| --- | --- |
| Glycerine | 20.0 |
| Hydroxyethyl cellulose | 1.3 |
| Sodium saccharin | 0.2 |
| Titanium dioxide | 0.5 |
| Sodium monofluorophosphate | 0.82 |
| Alpha alumina trihydrate | 31.5 |
| Calcined alumina | 20.0 |
| 1,6-di-(p-chlorophenyl biguanido) hexane digluconate (20% solution) | 4.723 |
| Berol 513 (pH 9.5) - (partially neutralized form) | 1.5 |
| Flavour | 1.0 |
| Water | Q.S. to 100 |

| Components | Parts |
|---|---|
| Dentifrice pH 8.1 | |

EXAMPLE 4

The following mouthwash having antibacterial activity and good foaming and flavour characteristics is prepared:

| Components | Parts |
|---|---|
| Ethanol | 15.0 |
| Sodium saccharine | 0.02 |
| Berol 513-fully neutralized form | 3 |
| 1,6-di-(p-chlorophenyl biguanido) hexane digluconate (20% solution) | 0.945 |
| Flavour | 0.218 |
| Dye (1% solution) | 0.6 |
| Water | Q.S. to 100 |
| Mouthwash pH 11.27 | |

When Berol 513, partially neutralized to pH 6 is employed, the mouthwash pH is 7.1.

EXAMPLE 5

The following dentifrice exhibits desirable antibacterialactivity and had good foaming characteristics:

| Components | Parts |
|---|---|
| Glycerine | 20.00 |
| Hydroxyethyl cellulose | 1.30 |
| Sodium saccharine | 0.2 |
| Alpha-alumina trihydrate | 52.00 |
| Benzalkonium chloride (50%) | 1.11 |
| Berol 513 (pH 6) - partially neutralized form | 1.65 |
| Flavour | 1.0 |
| Water | Q.S. to 100 |
| Dentifrice pH 8.7 | |

Desirable results are also obtained when 0.55 parts of undiluted benzethonium chloride are employed, the pH then being 8.6.

EXAMPLE 6

The following dentifrice exhibits desirable antibacterial activity and has good foaming characteristics:

| Components | Parts |
|---|---|
| Glycerine | 20.00 |
| Hydroxyethyl cellulose | 1.30 |
| Sodium saccharine | 0.2 |
| Alpha-alumina trihydrate | 52.00 |
| Cetrimide | 0.55 |
| Berol 513 (pH 6) - partially neutralized form | 1.65 |
| Flavour | 1.00 |
| Water | Q.S. to 100 |
| Dentifrice pH 8.6 | |

This dentifrice is also prepared using benzthonium chloride in place of Cetrimide.

The foregoing examples are given by way of illustration and variations thereof may be made without departing from the spirit of the ivention.

We claim:

1. An oral preparation comprising a dentally acceptable oral vehicle comprising a water-insoluble polishing material and dispersed in said vehicle a cationic antibacterial agent in amount of about 0.01-5% by weight based on the cationic portion thereof and about 0.05-5% by weight of an anionic phosphate ester surface active agent comprising a mixture of monoester of the formula

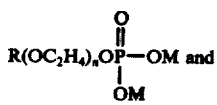

diester of the formula

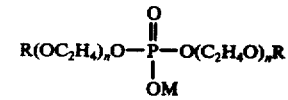

wherein R is an alkyl group of 10-20 carbon atoms, $n$ an integer from 1-6 and M is selected from the group consisting of hydrogen, alkali metal and ammonium, said oral preparation having a pH of at least about 6.

2. An oral preparation comprising a dentally acceptable oral vehicle comprising a water-alcohol mixture present in amount of about 70-99.9% by weight, the ratio of water being from 1:1 to 20:1, and dispersed in said vehicle a cationic antibacterial agent in amount of about 0.01-5% by weight based on the cationic portion thereof and about 0.05-5% by weight of an anionic phosphate ester surface active agent comprising a mixture of monoester of the formula

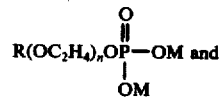

diester of the formula

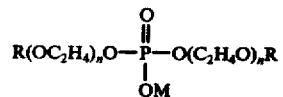

wherein R is an alkyl group of 10-20 carbon atoms, $n$ an integer from 1-6 and M is selected from the group consisting of hydrogen, alkali metal and ammonium, said oral preparation having a pH of at least about 6.

3. The oral preparation claimed in claim 1 wherein said cationic antibacterial agent is a quaternary ammonium compound.

4. The oral preparation claimed in claim 3 wherein said quaternary ammonium compound is benzethonium chloride.

5. The oral preparation claimed in claim 3 wherein said quaternary ammonium compound is a mixture of dodecyl, tetradecyl and hexadecyl trimethyl ammonium halide.

6. The oral preparation claimed in claim 1 wherein said cationic antibacterial agent is an amidine.

7. The oral preparation claimed in claim 6 wherein said amidine is 1,6-di-(p-chlorophenyl biguanido) hexane.

8. The oral preparation claimed in claim 1 wherein said cationic antibacterial agent is present in amount of about 0.05-1.0%.

9. The oral preparation claimed in claim 1 wherein R in in said anionic phosphate ester contains 16-18 carbon atoms.

10. The oral preparation claimed in claim 9 wherein said anionic phosphate ester contains a series of four ethylene oxide groups.

11. The oral preparation claimed in claim 1 wherein R in said anionic phosphate ester contains 10-18 carbon atoms and said anionic phosphate ester contains a series of five ethylene oxide units.

12. The oral preparation claimed in claim 1 wherein the ratio of mono-ester to di-ester in said anionic phosphate ester varies from about 1:10 to 10:1.

13. The oral preparation claimed in claim 1 wherein anionic phoshate ester is present in amount of about 0.5-30% by weight.

14. The oral preparation claimed in claim 1 wherein said polishing material is hydrated alumina.

15. The oral preparation claimed in claim 1 wherein said polishing material is present in amount of about 5-99% by weight.

* * * * *